United States Patent
Singh et al.

(10) Patent No.: US 8,987,328 B2
(45) Date of Patent: Mar. 24, 2015

(54) ESTERS OF CAPSAICINOIDS AS DIETARY SUPPLEMENTS

(75) Inventors: Chandra Ulagaraj Singh, San Antonio, TX (US); Rao Nulu Jagaveerabhadra, Austin, TX (US)

(73) Assignee: Trinity Laboratories, Inc., San Antonio, TX (US)

(*) Notice: Subject to any disclaimer, the term of this patent is extended or adjusted under 35 U.S.C. 154(b) by 194 days.

(21) Appl. No.: 12/589,887

(22) Filed: Oct. 30, 2009

(65) Prior Publication Data

US 2010/0120912 A1 May 13, 2010

Related U.S. Application Data

(60) Provisional application No. 61/109,762, filed on Oct. 30, 2008.

(51) Int. Cl.
| | | |
|---|---|---|
| A61K 31/23 | (2006.01) | |
| A61K 31/44 | (2006.01) | |
| A61K 9/48 | (2006.01) | |
| A61K 31/375 | (2006.01) | |
| A61K 45/06 | (2006.01) | |
| C07C 233/20 | (2006.01) | |
| A23L 1/30 | (2006.01) | |

(52) U.S. Cl.
CPC ............ *C07C 233/20* (2013.01); *A61K 9/4866* (2013.01); *A61K 31/23* (2013.01); *A61K 31/375* (2013.01); *A61K 45/06* (2013.01); *A23L 1/30* (2013.01)
USPC .......................................... 514/552; 514/282

(58) Field of Classification Search
CPC ................... A61K 2300/00; A61K 31/375
USPC .................................................. 514/552, 282
See application file for complete search history.

(56) References Cited

U.S. PATENT DOCUMENTS

| | | |
|---|---|---|
| 4,486,450 A | 12/1984 | Bernstein |
| 4,493,848 A | 1/1985 | LaHann et al. |
| 4,564,633 A | 1/1986 | LaHann et al. |
| 4,812,446 A | 3/1989 | Brand |
| 4,997,853 A | 3/1991 | Bernstein |
| 5,021,450 A | 6/1991 | Blumberg |
| 5,134,166 A | 7/1992 | Bernstein |
| 5,178,879 A | 1/1993 | Adekunle et al. |
| 5,290,816 A | 3/1994 | Blumberg |
| 5,403,868 A | 4/1995 | Reid et al. |
| 5,560,910 A | 10/1996 | Crandall |
| 5,741,510 A | 4/1998 | Rolf et al. |
| 5,762,963 A | 6/1998 | Byas-Smith |
| 5,827,886 A | 10/1998 | Hersh |
| 5,885,597 A | 3/1999 | Botknecht et al. |
| 5,889,041 A | 3/1999 | Anzalone |
| 5,910,512 A | 6/1999 | Conant |
| 5,916,565 A | 6/1999 | Rose et al. |
| 5,962,532 A | 10/1999 | Campbell et al. |
| 6,326,031 B1 | 12/2001 | Hsia et al. |
| 6,348,501 B1 | 2/2002 | Holt et al. |
| 6,573,302 B1 | 6/2003 | Holt et al. |
| 6,593,370 B2 | 7/2003 | Tamura et al. |
| 7,943,669 B2 | 5/2011 | Ebdrup |
| 8,765,807 B2 | 7/2014 | Singh et al. |
| 2001/0002406 A1 | 5/2001 | Robbins |
| 2002/0058048 A1 | 5/2002 | Tamura et al. |
| 2003/0082249 A1 | 5/2003 | Gordon |
| 2004/0146590 A1 | 7/2004 | Iadarola et al. |
| 2004/0224037 A1 | 11/2004 | Romero-Matos |
| 2005/0019436 A1 | 1/2005 | Burch et al. |
| 2006/0188590 A1 | 8/2006 | Ono |
| 2006/0269654 A1 | 11/2006 | Ali |
| 2007/0077316 A1 | 4/2007 | Morre et al. |
| 2007/0202200 A1 | 8/2007 | Astrup et al. |
| 2007/0212430 A1 | 9/2007 | Astrup et al. |
| 2008/0020996 A1 | 1/2008 | Singh et al. |
| 2008/0058362 A1* | 3/2008 | Singh et al. .................. 514/282 |
| 2009/0306225 A1* | 12/2009 | Lichter et al. .............. 514/772.1 |
| 2010/0120780 A1 | 5/2010 | Singh |
| 2011/0039875 A1 | 2/2011 | Singh |
| 2013/0189354 A1 | 7/2013 | Singh |
| 2014/0134261 A1 | 5/2014 | Singh et al. |

FOREIGN PATENT DOCUMENTS

EP 0149545 A2 7/1985

OTHER PUBLICATIONS

Fang et al., In vivo percutaneous absorption of capsaicin, nonivamide, and sodium nonivamide acetate from ointment bases: skin erythema test and non-invasive surface recovery technique in humans, International Journal of Pharmaceutics, 131:143-151 (1996).
Office Action from U.S. Appl. No. 13/108,419, mailed Jun. 26, 2014.
Office Action from U.S. Appl. No. 13/108,419, mailed Dec. 11, 2012.
Office Action from U.S. Appl. No. 13/108,419, mailed Apr. 13, 2012.
Office Action from U.S. Appl. No. 13/108,419, mailed Oct. 28, 2011.
Office Action from U.S. Appl. No. 11/878,335, mailed Dec. 22, 2010.
Office Action from U.S. Appl. No. 11/878,335, mailed Jul. 9, 2010.

* cited by examiner

*Primary Examiner* — Shirley V Gembeh
(74) *Attorney, Agent, or Firm* — Nevrivy Patent Law Group P.L.L.C.

(57) ABSTRACT

Provided are nutraceutical or dietary supplemental compositions comprising esterified capsaicinoids. The esterified capsaicinoids may converted to the active parent capsaicinoid compound following enzymatic or chemical hydrolysis. In various embodiments, these esterified capsaicinoids have a higher lipophilicity, lipid solubility and result in less irritation to the stomach than the parent capsaicinoid, and hence may be included in certain dietary supplement formulations, including capsules, pills and tablets dietary supplement formulations. The dietary supplement compositions may be used for pain management in mammals in vivo and/or in the treatment of various pathological conditions in humans.

17 Claims, No Drawings

ESTERS OF CAPSAICINOIDS AS DIETARY SUPPLEMENTS

This application claims the benefit of the U.S. Provisional Application No. 61/109,762 filed Oct. 30, 2008, and the text of application 61/109,762 is incorporated by reference in its entirety herewith.

FIELD OF INVENTION

This invention relates to dietary supplements. More specifically it relates to the use of esters of capsaicin as dietary supplement.

BACKGROUND OF THE INVENTION

*Capsicum* consists of the dried ripe fruits of *Capsicum annuum* Roxb. (Family Solanaceae), a small erect shrub indigenous to tropical America, cultivated in South America, China, India and Africa. *Capsicum* contains a crystalline pungent principle capsaicin, traces of a liquid alkaloid, red coloring matter and a fatty oil. In folk medicine, *Capsicum* is regarded as an aphrodisiac, depurative, digestive, stomachic, carminative, antispasmodic, diaphoretic, antiseptic, counter-irritant, rubefacient, stypic, and tonic. Internally, *Capsicum* has been used to treat asthma, pneumonia, diarrhea, cramps, colic, toothache, flatulent dyspepsia without inflammation; insufficiency of peripheral circulation; as a gargle for sore throat, chronic pharyngitis and laryngitis; and externally as a lotion or ointment to treat neuralgia, including rheumatic and arthritic pain, and unbroken chilblains (cold injuries) (Duke, 1985; Leung and Foster, 1996; Newall et al., 1996).

In Germany, cayenne pepper is official in the *German Pharmacopeia* and approved in the Commission E monographs as a topical ointment for the relief of painful muscle spasms in the upper torso (DAB, 1997). In the United States, *Capsicum* tincture and oleoresin were formerly official in the *United States Pharmacopeia* and *National Formulary*. *Capsicum* USP was used as a carminative, stimulant, and rubefacient (Leung and Foster, 1996; Taber, 1962).

The most potent and predominant chemical entity in *Capsicum* is capsaicin (0.14%) (Cordell and Araujo, 1993; Figure 1). The heat sensation of pure capsaicin is approximately 16 million Scoville heat units (SHU) and can, when diluted one-hundred-thousand fold in its pure form, cause blistering of the tongue. The heat sensation of pure dihydrocapsaicin and nordihydrocapsaicin is approximately 9 million Scoville heat units (SHU). A series of homologous branched- and straight-chain alkyl vanillylamides, collectively known as capsaicinoids, is present in lesser concentrations than the parent compound, capsaicin. Of the capsaicinoid fraction, capsaicin (48.6%) is quantitatively followed by 6,7-dihydrocapsaicin (36%), nordihydrocapsaicin (7.4%), homodihydrocapsaicin (2%), and homocapsaicin (2%) (Duke, 1985). Capsaicinoids and capsaicin are collectively found in amounts of 0.1% to 1%, with quantities varying according to soil and climate (Rumsfield and West, 1991).

Capsaicin, a colorless crystalline substance, was first synthesized in 1930. Capsaicin has been studied since the mid-19th century and its structure is elucidated as 8-methyl-6-nonenoyl vanillylamide (Cordell and Araujo, 1993). Most pharmacological studies performed with isolated constituents of chile pepper have focused on capsaicin, which is the major pungent constituent.

The crude extract of *Capsicum* fruits, known as *Capsicum* oleoresin, contains at least 100 different volatile chemical constituents, and therefore may function in differing ways from pure capsaicin. Thus, it is important to distinguish between studies using capsaicin and those employing *Capsicum* oleoresin (Cordell and Araujo, 1993).

Nonivamide (pelargonic acid vanillylamide) is a common synthetic adulterant of *Capsicum* products. Although structurally different from capsaicin, its presence in *Capsicum* or capsaicin samples can be detected spectrographically and there is no evidence that this compound occurs naturally in *Capsicum* (Cordell and Araujo, 1993).

It has been shown that capsaicin added to meals increased sympathetic nervous system activity and energy metabolism (Yoshioka et al., 1999; Yoshioka et al., 1998; Lejeune et al., 2003). However, there are some inconsistencies about the effect of capsaicin on the substrate oxidation (Yoshioka et al., 1995; Lim et al., 1997).

Capsaicin affects lipid metabolism as demonstrated in a study by Kawada et al. (1986). Male rats fed a diet containing 30% lard with capsaicin at 0.14% of the diet developed serum triglyceride levels that were significantly lower than those of animals receiving a high-fat diet without capsaicin. But levels of free fatty acids, cholesterol, and pre-beta-lipoprotein were not affected. Activities of liver enzymes involved in lipid synthesis (acetyl-CoA carboxylase) and in carbohydrate metabolism (glucose-6-phosphate dehydrogenase) were inhibited in the high-fat diet, but the activity of the latter was restored to control levels by the added dietary capsaicin. The weight of perirenal adipose tissue was reduced in a dose-dependent manner by capsaicin. These results suggested that capsaicin did not interfere with lipid biosynthesis. Rather, that capsaicin might stimulate lipid metabolism, and possibly facilitates mobilization of lipid from adipose tissue.

In a follow-up to the study above, Kawada et al. (1986a) measured the effect of i.p. administered capsaicin on general energy metabolism, including oxygen consumption, respiratory quotient, and substrate utilization. Capsaicin had a general stimulatory effect on metabolism, similar to that of epinephrine; oxygen consumption was elevated, respiratory quotient was initially elevated, then decreased; and serum glucose and insulin levels were elevated, concomitant with a rapid decrease in liver glycogen, and a gradual increase in serum triglycerides. The response was blocked by beta-adrenergic blockers, but was not effected by alpha-adrenergic or ganglion blockers. Their results suggested that capsaicin effects metabolism either as a direct beta-adrenergic agonist, or indirectly by stimulating catecholamine release.

Yamato et al. (1996) showed that capsaicin produced a marked concentration-dependent decrease in the amplitude, the rate of rise, and the rate of relaxation of the contractile tension of rat ventricular papillary muscles; however, the half-life of the relaxation and the time to peak tension were only slightly effected. Calcium release and shortening of action potential duration in ventricular myocytes was profoundly reduced by capsaicin, perhaps resulting from the non-specific membrane-stabilizing effects of capsaicin.

Capsaicin treatment caused a biphasic effect on contractile force, left ventricular systolic blood pressure, and heart rate of isolated perfused rat hearts. A transient initial increase in contractile force and left ventricular systolic pressure was observed, followed by a prolonged depression of both parameters. Heart rate was increased, but this effect was not followed by a subsequent reduction. The initial increases in contractile force and blood pressure could have been induced by the release of calcitonin-gene-related peptide (CGRP) from local sensory nerves; the negative inotropic effects following the initial increase may be due to a direct inhibitory effect of capsaicin on ventricular cells, or to nonspecific membrane-stabilizing effects. The increased heart rate was attributed to the release of CGRP (Lundberg 1985).

Capsaicin elicits a vasoconstrictive response in the large cerebral arteries of the cat (Saito et al., 1988), and in the middle and basilar cerebral arteries, an effect was attributed to a direct contraction of smooth muscle, since the response was independent of the presence of endothelium and nerve components. However, Saito et al. found results suggesting that while capsaicin releases and depletes vasodilator peptides from perivascular nerves, the direct vasoconstrictor effects of capsaicin overwhelm the vasodilator effects of these peptides.

An increased activity of CGRP-containing trigeminovascular nerve fibres has been correlated to the pathophysiology of migraine (Buzzi et al., 1991) either during attacks (Goadsby et al., 1990; Goadsby & Edvinsson, 1993) or as a general imbalance in migraine patients (Ashina et al., 2000). Therefore, clinical potentials of CGRP receptor-antagonists in the treatment of migraine have been addressed (Doods et al., 2000). Capsaicin (Holzer, 1991b; Szallasi & Blumberg, 1999) potently and selectively causes release of CGRP from sensory nerve terminals both in vitro and in vivo (Duckles & Levitt, 1984; Duckles, 1986; Holzer, 1991a; Saito & Goto, 1986; Wharton et al., 1986). The mechanism of capsaicin-induced CGRP depletion involves binding of capsaicin to vanilloid 1 receptors (VR1) (Caterina et al., 1997). Capsaicin-association to VRs triggers Ca2+ influx and elevated intracellular calcium levels in turn stimulate CGRP-release. The vanilloid 1 receptor is in addition to capsaicin stimulated by heat, hydrogen ions, lactate (Franco-Cereceda & Liska, 2000; Franco-Cereceda, 1988) and the endogeneous cannabinoid, anandamide (Zygmunt et al., 1999). Capsaicin is thought to activate the sympathetic nerves via vanilloid receptor 1 (VR-1) by stimulating the release of NE into the synaptic cleft (Caterina et al., 2000; Vogel 2000).

A hypoxic reflectory release of CGRP which has been suggested in myocardium (Kallner, 1998; Dai et al., 2000; Franco-Cereceda & Liska, 2000) and in cerebral arteries (McCulloch et al., 1986) may be due to stimulation of this receptor as well. It has previously been demonstrated that CGRP, rather than SP and NKA, is responsible for the capsaicin-induced vasodilatation of guinea-pig basilar artery (Franco-Cereceda & Rudehill, 1989; O'Shaughnessy et al., 1993; Jansen-Olesen et al., 1996).

In tests using cultured human intestinal epithelial cells, Jensen-Jarolim et al. (1998) found sufficient in vitro evidence to suggest that *Capsicum* may increase the permeability of the gastrointestinal tract to allow transport of macromolecules and ions across the epithelium; an effect, they add, that might have importance to food intolerance and allergic reactions to food. The stimulatory effect of orally administered capsaicin on gastric acid secretion and mucosal blood flow was studied in rats using amounts roughly equivalent to a normal That diet. Capsaicin was noted to have a protective effect on gastric mucosa of ethanol-induced gastric lesions in rats (Uchida et al., 1991). The protective effect was attenuated upon pretreatment with indomethacin and disappeared in capsaicin-sensitive nerve-degenerated rats, suggesting that enhanced prostaglandin formation inhibited lesion formation. Further study by the same group found decreased stomach motility and increased mucosal blood flow with intragastric capsaicin treatment, whereas capsaicin pre-treatment desensitized the afferent neurons, thereby mitigating this protective effect.

An in vitro chemopreventive activity of capsaicin was shown by Morr et al. (1995). When capsaicin was added to cultured cells of Caov-3 human ovarian carcinoma, MCF-10A human mammary adenocarcinoma, HL-60 human pro-myelocytic leukemia, and HeLa cells, a preferential growth-inhibition was evident as cells became smaller and underwent cell death. Condensed and appearing fragmented, the nuclear DNA of these cells suggested that capsaicin had induced apoptosis.

Capsaicin has a profound antiproliferative effect on prostate cancer cells (Mori 2006), inducing the apoptosis of both androgen receptor (AR)-positive (LNCaP) and -negative (PC-3, DU-145) prostate cancer cell lines associated with an increase of p53, p21, and Bax. Capsaicin down-regulated the expression of not only prostate-specific antigen (PSA) but also AR. Promoter assays showed that capsaicin inhibited the ability of dihydrotestosterone to activate the PSA promoter/enhancer even in the presence of exogenous AR in LNCaP cells, suggesting that capsaicin inhibited the transcription of PSA not only via downregulation of expression of AR, but also by a direct inhibitory effect on PSA transcription. Capsaicin inhibited NF-K activation by preventing its nuclear migration. In further studies, capsaicin inhibited tumor necrosis factor-A-stimulated degradation of IKBA in PC-3 cells, which was associated with the inhibition of proteasome activity. Taken together, capsaicin inhibits proteasome activity which suppressed the degradation of IKBA, preventing the activation of NF-KB. Capsaicin, when given orally, significantly slowed the growth of PC-3 prostate cancer xenografts as measured by size [75 F 35 versus 336 F 123 mm3 (FSD); P=0.017] and weight [203 F 41 versus 373 F 52 mg (FSD); P=0.0006; capsaicin-treated versus vehicle treated mice, respectively]. These data suggests that capsaicin, or a related analogue, may have a role in the management of prostate cancer.

The arachidonic acid cascade is an important component of inflammation and the associated localized immune response. The release of arachidonic acid (AA) from membrane phospholipids and subsequent leukotriene biosynthesis occurs during inflammation, and products formed by AA oxidation act in concert with numerous other factors, including cytokines, PAF (platelet-activating factor), nitrogen oxide, and histamine, all of which are important mediators of the immune response. A study (Panossian et al., 1996) found that at low concentrations capsaicin stimulated the production of interleukin-1a, while at higher doses it inhibited this response. Capsaicin caused a dose-dependent release of AA from PMNs (poly-morphonuclear leukocytes), and a similar concentration-dependent conversion of the AA metabolites, prostaglandin E2 (PGE2) and LTB4. When incubated with granulocytes, capsaicin caused an increased synthesis of 12-HETE, an eicosanoid metabolite of AA, but at the same time was found to cause a dose-dependent decrease of all products of 5-lipoxygenase. These results suggested that the dose-dependent reversible effects of capsaicin on immune cells and interleukin-1alpha are closely associated with arachidonic acid metabolism (Panossian et al., 1996).

Viral replication, immune regulation, and induction of various inflammatory and growth-regulatory genes require activation of a nuclear transcription factor (NF)-κ-B. Agents that can block NF-κ-B activation have potential to block downstream responses mediated through this transcription factor. Capsaicin (8-methyl-N-vanillyl-6-nonenamide) has been shown to regulate a wide variety of activities that require NF-κ-B activation (Singh 1996). The pretreatment of human myeloid ML-1a cells with capsaicin blocked TNF-mediated activation of NF-κ-B in a dose- and time-dependent manner. Capsaicin treatment of cells also blocked the degradation of I-κ-B alpha, and thus the nuclear translocation of the p65 subunit of NF-κ-B, which is essential for NF-κ-B activation. TNF-dependent promoter activity of I-κ-B alpha, which contains NF-κ-B binding sites, was also inhibited by capsaicin.

The effects of capsaicin and dihydrocapsaicin on blood lipid and lipoprotein concentrations were determined in two groups of turkeys (Negulesco 1987). The first group was maintained on a cholesterol-free diet, while the second received a diet supplemented with 0.2% cholesterol. Daily administration of capsaicinoids occurred at a dose of 4 mg per animal. Neither drug had an effect on serum triglyceride concentrations in the animals receiving the cholesterol-free diet. However, total cholesterol, LDL-cholesterol and HDL-cholesterol concentrations were increased significantly, while VLDL cholesterol concentrations were decreased significantly by both drugs relative to controls. In the cholesterol-fed group triglycerides, total cholesterol and LDL-cholesterol decreased significantly with dihydrocapsaicin treatment. Both compounds reduced VLDL-cholesterol and increased HDL-cholesterol in the cholesterol-fed animals. Dihydrocapsaicin had a greater efficacy in producing beneficial anti-hyperlipidemic effects in the cholesterol-fed animals.

*Capsicum frutescens* has been used to treat diabetes mellitus by traditional healers in Jamaica (Tolan 2004). Purification experiments employing thin layer chromatography (TLC) and high performance liquid chromatography led to the extraction of the active principle, capsaicin. Purified capsaicin caused a decrease in blood glucose levels to 4.91+/−0.52 (n=6) mmol/dL versus 6.40+/−0.13 mmol/dL (n=6) for the control (p<0.05) at 2.5 h in an OGTT in dogs. There was a concomitant elevation in plasma insulin levels (p<0.05). In conclusion, it can be stated that capsaicin is the major constituent of *Capsicum frutescens* that is responsible for the hypoglycaemic episodes seen in the dogs. It is also apparent that the latter is mediated by insulin release.

Neurogenic inflammation has been successfully modeled using capsaicin. When injected intradermally, capsaicin evokes a temporary burning sensation lasting 3 to 5 minutes and a characteristic localized flare consisting of a red flush with slight edema (Holzer 1988). The capsaicin flare is thought to be induced by a local axon reflex involving release of neuropeptides such as SP and CGRP from sensory neurons (Holzer 1988). Additional mediators of the capsaicin flare are thought to include cytokines, prostaglandins, and other neuropeptides (Holzer 1991; Veronesi 1999). Within normal individuals, the size of the capsaicin flare over time is quite consistent (Jolliffe 1995).

The effect of glucocorticoids and catecholamines on the capsaicin-induced flare have been minimally examined. However, glucocorticoids have not been shown to block the capsaicin-induced flare (Ahluwalia 1994). Alpha adrenoreceptors are known to be involved in the pain response to capsaicin (Kinnman 1997).

Depending on the concentration used and the mode of application, capsaicin can selectively activate, desensitize, or exert a neurotoxic effect on small diameter sensory afferent nerves while leaving larger diameter afferents unaffected (Holzer, 1991; Winter et al., 1995). Sensory neuron activation occurs due to interaction with a ligand-gated nonselective cation channel termed the vanilloid receptor (VR-1) (Caterina et al., 1997), and receptor occupancy triggers $Na^+$ and $Ca^{2+}$ ion influx, action potential firing, and the consequent burning sensation associated with spicy food or capsaicin-induced pain. VR1 receptors are present on both C and Ab fibers, and can be activated by capsaicin and its analogs, heat, acidification, and lipid metabolites (Tominaga et al., 1998; Caterina and Julius, 2001). Desensitization occurs with repeated administration of capsaicin, is a receptor-mediated process, and involves $Ca^{2+}$- and calmodulin-dependent processes and phosphorylation of the cation channel (Winter et al., 1995; Wood and Docherty, 1997).

Capsaicin induces release of substance P and calcitonin gene-related peptide from both peripheral and central terminals of sensory neurons, and desensitization inhibits such release (Holzer, 1991); such inhibition may result from inhibition of voltage-gated $Ca^{2+}$-currents (Docherty et al., 1991; Winter et al., 1995). Neurotoxicity is partially osmotic and partially due to $Ca^{2+}$ entry with activation of $Ca^{2+}$-sensitive proteases (Wood et al., 1989; Winter et al., 1995). In neonates, neurotoxicity can be lifelong (Janscó et al., 1977), whereas in adult animals receiving a localized dose, a reversible injury may occur as cell bodies capable of regeneration are left intact (Holzer, 1991). Both desensitization and neurotoxicity lead to analgesia in rodent paradigms, with specific characteristics of analgesia depending on the dose of capsaicin, route of administration, treatment paradigm (i.e., acute or repeated administration), and age of the animal (Holzer, 1991; Winter et al., 1995). The topical skin application of capsaicin to rodents produces analgesia (Kenins, 1982; Lynn et al., 1992), but variability in outcome can occur due to the concentration, the number of applications, and the different vehicles used that can affect the rate and extent of skin penetration (Carter and Francis, 1991; McMahon et al., 1991).

The distribution and metabolism of capsaicin and/or dihydrocapsaicin has been studied in rats. Capsaicin is distributed to the brain, spinal cord, liver and blood within 20 mins. of i.v. administration. Oral doses of dihydrocapsaicin in the rat showed metabolic activity associated with its absorption into the portal vein. Capsaicin and dihydrocapsaicin are metabolized in the liver by the mixed-function oxidation system (cytochrome P-450 dependent system). It is assumed that capsaicin is excreted in urine. In rats, most of dihydrocapsaicin is known to be rapidly metabolized and excreted in the urine (Rumsfield and West, 1991).

Acute intradermal injection of capsaicin to the skin in humans produces a burning sensation and flare response; the area of application becomes insensitive to mechanical and thermal stimulation, the area of flare exhibits a primary hyperalgesia to mechanical and thermal stimuli, and an area beyond the flare exhibits secondary allodynia (Simone et al., 1989; LaMotte et al., 1991). Repeated application to normal skin produces desensitization to this response and thus forms the basis of the therapeutic use of topical capsaicin in humans. Desensitization involves both physiological changes in the terminals of the sensory neuron noted above, as well as a degree of loss of sensory fiber terminals within the epidermis (Simone et al., 1989; Nolano et al., 1999). With respect to topical applications of capsaicin, it has been estimated that assuming 100% of a topically-applied dose is absorbed into the body, an application of 90 g capsaicin (2 tubes of cream, 0.025% capsaicin) per week would result in a daily exposure of 0.064 mg/kg capsaicin for a 50 kg person. This represents less than 10% of the dietary intake of a typical Indian or That diet (Rumsfield and West, 1991).

Topical capsaicin preparations of 0.025 and 0.075% are available for human use, and these produce analgesia in randomized double-blind placebo-controlled studies, open label trials, and clinical reports (Watson, 1994; Rains and Bryson, 1995). Capsaicin, is recognized by the U.S. FDA as a counterirritant for use in OTC topical analgesic drug products (Palevitch and Craker, 1995). It is used as a component in various counterirritant preparations (Leung and Foster, 1996), including ArthriCare® (Del Pharmaceuticals, Inc.) arthritis pain relieving rub, which contains *Capsicum* oleoresin (0.025% capsaicin) in combination with menthol USP and *Aloe vera* gel (Arky et al., 1999). *Capsicum* ointments, such as Zostrix® cream (GenDerm Corp.), containing 0.025% or 0.075% capsaicin, are used topically to treat shingles (herpes zoster) and post-herpetic neuralgia (Bernstein et al., 1987; Der Marderosian, 1999; Palevitch and Craker, 1995).

Topical capsaicin produces benefit in post-herpetic neuralgia (Bernstein et al., 1989; Watson et al., 1993), diabetic neuropathy (Capsaicin Study Group, 1992), postmastectomy pain syndrome (Watson and Evans, 1992; Dini et al., 1993), oral neuropathic pain, trigeminal neuralgia, and temperomandibular joint disorders (Epstein and Marcoe, 1994; Hersh et al., 1994), cluster headache (following intranasal application; Marks et al., 1993), osteoarthritis (McCarthy and McCarthy, 1992), and dermatological and cutaneous conditions (Hautkappe et al., 1998). Whereas pain relief is widely observed in these studies, the degree of relief is usually modest, although some patients have a very good result. Topical capsaicin is generally not considered a satisfactory sole therapy for chronic pain conditions and is often considered an adjuvant to other approaches (Watson, 1994). No significant benefit was reported in chronic distal painful neuropathy (Low et al., 1995) or with human immunodeficiency virus-neuropathy (Paice et al., 2000).

Capsaicin produces marked alterations in the function of a defined subpopulation of unmyelinated sensory afferents, termed C-polimodal nociceptors. Following the initial period of intense burning or stinging pain accompanied by erythema, topical capsaicin application causes insensitivity to further irritation by a variety of noxious stimuli. Accordingly, topical preparations of capsaicin find use as a topical therapy for a variety of cutaneous disorders that involve pain and itching, such as post-herpetic neuralgia, diabetic neuropathy, pruritus, psoriasis, cluster headache, postmastectomy pain syndrome, rhinopathy, oral mucositis, cutaneous allergy, detrusor hyperreflexia, loin pain/hematuria syndrome, neck pain, amputation stump pain, reflex sympathetic dystrophy, pain due to skin tumor and arthritis (Hautkappe et al., 1998).

The most frequently encountered adverse effect with capsaicin is burning pain at the site of application, particularly in the first week of application. This can make it impossible to blind trials and can lead to dropout rates ranging from 33 to 67% (Watson et al., 1993; Paice et al., 2000). Another factor in compliance is the time delay before therapeutic effect is observed (at least a week, but sometimes several weeks). One approach toward minimizing adverse effects and accelerating the rate of analgesia has been to deliver a higher capsaicin concentration (5-10%) under regional anesthesia, and this produced sustained analgesia lasting 1 to 8 weeks in cases of complex regional pain syndrome and neuropathic pain (Robbins et al., 1998). When topical local anesthetics were applied with 1% topical capsaicin, no alteration in pain produced by the capsaicin was observed in healthy subjects (Fuchs et al., 1999) indicating that this co-treatment was not sufficient to block the pain induced by capsaicin.

Because of intense burning or stinging pain, many patients are not tolerated in the long-term treatment with topical capsaicin and, therefore, have to discontinue the treatment before appearance of analgesic effect of capsaicin through prolonged administration. It was reported that 26 out of 39 (66.7%) patients suffering from post-herpetic neuralgia were not tolerated with a 0.025% capsaicin preparation (Zostrix, Gen Derm, USA). With a 0.075% preparation (Zostrix-HP, Gen Derm, USA), 5 out of 16 (31.3%) and 45 out of 74 (60.8%) patients with post-herpetic neuralgia were not tolerated (Peikert et al., 1991; Watanabe et al., 1994; Bernstein et al., 1989 and Watson et al., 1993).

Various capsaicin compositions have been developed over the years, in particular, the psoriatic composition of U.S. Pat. No. 4,486,450, the nasal composition of U.S. Pat. No. 5,134,166, and the composition of U.S. Pat. No. 4,997,853, the anti-inflammatory composition of U.S. Pat. No. 5,560,910, the composition of U.S. Pat. No. 5,962,532, the composition for animals of U.S. Pat. No. 5,916,565, the stomach treatments of U.S. Pat. No. 5,889,041, the composition of U.S. Pat. No. 5,827,886, the patch with medication of U.S. Pat. No. 5,741,510, all of which are incorporated by reference herein.

U.S. Pat. No. 6,593,370 discloses a topical capsaicin preparation for the treatment of painful cutaneous disorders and neural dysfunction. The preparation contains a nonionic, amphoteric or cationic surfactant in an amount effective to eliminate or substantially ameliorate burning pain caused by capsaicin.

U.S. Pat. No. 6,573,302 discloses a cream comprising: a topical carrier wherein the topical carrier comprises a member selected from the group comprising lavender oil, myristal myristate, and other preservatives including, hypericum perforatum arnica montana capric acid; and 0.01 to 1.0 wt. % capsaicin; 2 to 10 wt. % an encapsulation agent selected from the group comprising colloidal oatmeal hydrogenated lecithin, dipotassium glycyrlhizinate and combinations thereof; esters of amino acid; a light scattering element having a particle size up to 100 nm.; and a histidine.

U.S. Pat. No. 6,348,501 disclose a lotion for treating the symptoms of arthritis using capsaicin and an analgesic, and a method for making.

U.S. Pat. No. 5,962,532 disclose methods and compositions for treating pain at a specific site with an effective concentration of capsaicin or analogues. The methods involve providing anesthesia to the site where the capsaicin or analogues thereof is to be administered, and then administering an effective concentration of capsaicin to the joint. The anesthesia can be provided directly to the site, or at remote site that causes anesthesia at the site where the capsaicin is to be administered. For example, epidural regional anesthesia can be provided to patients to which the capsaicin is to be administered at a site located from the waist down. By pretreating the site with the anesthetic, a significantly higher concentration of capsaicin can be used. Effective concentrations of capsaicin or analogues thereof range from between 0.01 and 10% by weight, preferably between 1 and 7.5% by weight, and more preferably, about 5% by weight. This provides for greater and more prolonged pain relief, for periods of time ranging from one week to several weeks. In some cases the pain relief may be more sustained because the disease that underlies the pain may improve due to a variety of factors including enhancement of physical therapy due to less pain in the soft tissues which may foster enhanced mobilization of soft tissues, tendons, and joints.

U.S. Pat. No. 5,910,512 disclose a water-based topical analgesic and method of application wherein the analgesic contains *Capsicum, Capsicum* oleoresin and/or capsaicin. This analgesic is applied to the skin to provide relief for rheumatoid arthritis, osteoarthritis, and the like.

U.S. Pat. No. 5,403,868 discloses novel capsaicin derivatives containing thio-urea, processes for the production thereof, dietary supplemental compositions containing them and use thereof as pharmaceuticals.

U.S. Pat. No. 5,178,879 discloses clear, water-washable, non-greasy gels useful for topical pain relief contain capsaicin, water, alcohol and a carboxypolymethylene emulsifier. A method of preparing the gels is also disclosed U.S. Pat. No. 5,021,450 relates to a new class of compounds having a variable spectrum of activities for capsaicinlike responses, compositions thereof, processes for preparing the same, and uses thereof. Compounds were prepared by combining phorbol related diterpenses and homovanillac acid analogs via esterification at the exocyclic hydroxy group of the diterpene. Examples of these compounds include 20-homovanillyl-mezerein and 20-homovanillyl-12-deoxyphorbol-13-phenyl acetate.

U.S. Pat. No. 4,997,853 discloses a method and composition for treating superficial pain syndromes which incorporates capsaicin in a therapeutically effective amount into a pharmaceutically acceptable carrier and adding to this composition a local anesthetic such as lidocaine or benzocaine. The composition containing the anesthetic is then applied to the site of the pain. A variation on the treatment includes initial treatment with the composition containing the local anesthetic until the patient has become desenstitized to the presence of capsaicin and subsequent treatment with a composition ommitting the local anesthetic.

US application 20050019436 provides compositions and methods for relieving pain at a site in a human or animal in need thereof by administering at a discrete site in a human or animal in need thereof a dose of capsaicin in an amount effective to denervate a discrete site without eliciting an effect outside the discrete location, the dose of capsaicin ranging from 1 μg to 3000 μg.

US application 20040224037 claims a use of Capsaicin (8-methyl-n-vanillyl-6-nonenamide), its derivatives, vanilloids and *Capsicum* extract, to combat and control HIV (humans immunodeficiency virus) and AIDS (acquired immunodeficiency syndrome). An evaluation of a *Capsicum* sp consumption of a long term AIDS survivors group permitted a definition of more efficacious ways to administer the substance. Capsaicin intravenous and by subcutaneous or intramuscular administration at low concentration implemented by using infuses, inhibits HIV replication and stimulates the production and proliferation of lymphocytes and cells NK. Also it acts as desinfectant in macrophages, and has a power as anticancer and antioxidant agent. Moreover has the property to control and annihilate common opportunistic illnesses related to HIV due to its triple antibiotic characteristics.

US application 20040146590 provides methods and kits for the selective ablation of pain-sensing neurons. The methods comprise administration of a vanilloid receptor agonist to a ganglion in an amount that causes death of vanilloid receptor-bearing neurons. Accordingly, the present invention provides methods of controlling pain and inflammatory disorders that involve activation of vanilloid receptor-bearing neurons.

US application 20030133995 discloses a chemical composition for an ingestible capsaicin neutralizer to neutralize the effect of capsaicin on the oral cavity, tongue, and esophagus when capsaicin from hot peppers is ingested by a user comprised of an effective neutralizing amount of casein protein, or the salt thereof, an alkali earth metal halide, and the balance water.

US application 20030082249 discloses a composition for use in treating or preventing mucositis, and/or xerostomia, including capsaicin or capsaicin derivative, and one or more additional compounds useful in treating mucositis and/or xerostomia, wherein the composition is provided in an oral delivery vehicle. The term capsaicin derivative and capsaicinoid as used in the disclosure are interchangeable and generally refer to capsaicin analogs. Among the capsaicinoids useful in the practice of the disclosure are capsaicin, the N-phenylmethylalkenamide capsaicin derivatives; dihydrocapsaicin; norhydrocapsaicin; nordihydrocapsaicin; homocapsaicin; homohydrocapsaicin; homodihydrocapsaicin; civamide (cis-capsaicin); nonivamide; NE-19550 (N-[4-hydroxy-3-methoxyphenyl)methyl-1]-9Z-octadecanamide) (olvanil); NE-21610 (N-[(4-(2-aminoethoxy)-3-methoxyphenyl)methyl]-9Z-octadecanamide) Sandoz Pharmaceutical Corp, East Hanover, N.J.); NE-28345 (N-(9Z-octadecenyl)-3-methoxy-4-hydroxyphenylacetamide; also known as N-oleyl-homovanillamide); and their analogs and derivatives (U.S. Pat. No. 5,762,963, which is incorporated herein by reference). NE-19550, NE-21610, and NE-28345 are discussed in Dray et al. (1990).

US application 20020058048 discloses a topical capsaicin preparation for the treatment of painful cutaneous disorders and neural dysfunction is disclosed. The preparation contains a nonionic, amphoteric or cationic surfactant in an amount effective to eliminate or substantially ameliorate burning pain caused by capsaicin.

US application 20010002406 discloses transdermal application of capsaicin (or a capsaicin analog) in a concentration from greater than about 5% to about 10% by weight to be an extremely effective therapy for treating neuropathic pain, so long as an anesthetic, preferably by means of a transdermal patch, is administered initially to the affected area to minimize the expected side effects from subsequent capsaicin application. Analogs of capsaicin with physiological properties similar to capsaicin are known (Ton 1955). For example, resiniferatoxin is described as a capsaicin analog by Blumberg, U.S. Pat. No. 5,290,816. U.S. Pat. No. 4,812,446, describes capsaicin analogs and methods for their preparation.

U.S. Pat. Nos. 4,493,848 and 4,564,633 disclose the derivatives of capsaicin, including short chain ester derivatives (C1-C6) of capsaicin for analgesia in human.

US applications 20070202200 and 20070212430 disclose a composition for reducing the weight of a human. The composition is provided in the form of a capsule comprising an effective amount of capsaicin and/or analogs thereof, L-tyrosine, supplemental caffeine and/or and analogs thereof, green tea extract containing catechin and caffeine, and embodiments which include calcium. The disclosure is also directed toward methods for reducing and maintaining weight of a human using the composition.

US application 20060188590 relates to a composition that includes two compounds selected from a group of nine members, i.e., an .alpha.-glucosidase inhibitor, an intestinal glucose transporter inhibitor, a glycation inhibitor, a nitric oxide production inhibitor, an aldose reductase inhibitor, a PPAR agonist, an adipocytokine activator, a glucose uptake enhancer, and a thermogenesis enhancer, in which the two compounds are two different members; and each compound is naturally occurring in a plant and is provided in the form of a plant extract. The thermogenesis inhibitor includes capsaicin. This disclosure also relates to a method of treating diabetes or obesity with the above-mentioned composition.

U.S. Pat. No. 6,326,031 relates to nutritional supplements to the human diet used to increase levels of HDL, and decrease levels of O-LDL, cholesterol, and triglycerides in human blood plasma. More specifically, the disclosure teaches novel nutritional supplements which contain a novel combination of fish oil, garlic, rutin, and capsaicin, as well as methods of preparing the nutritional supplements.

US application 20070077316 discloses compositions comprising a vanilloid and tea catechins in amounts and proportions which combat virus infections in a human or animal. The vanilloid can be provided in the form of a dried pepper preparation and the tea catechins can be provided in the form of a green tea extract (or concentrate). These active ingredients can be provided separately or in combination. The administration of a such nutritional or other composition, desirably oral administration (in an amount effect) results in reduced virus infection or ameliorated symptoms of virus infection in a human or an animal in need of such a composition.

US application 20060269654 discloses a consumable sexual performance aid comprising edible strip substrate coated with at least one sexual performance-enhancing ingredient. The ingredient may be natural or may comprise a pharmaceutical.

A need exists for a oral preparation which eliminates or substantially ameliorates initial stinging pain in the stomach caused by capsaicin observed in the administration thereby making the preparation tolerable in long-term administration.

The purpose of the present application is to disclose the unexpected discovery that esters of capsaicin have significantly less burning pain at the stomach when taken orally as a dietary supplement. The present invention does not rely on coating capsaicin for oral consumption to reduce the burning sensation in the stomach.

SUMMARY OF THE INVENTION

The present invention provides for certain novel dietary compositions containing ester derivatives of capsaicin that are highly lipophilic. The compounds of capsaicin set forth herein are enzymatically cleaved to the parent compound in the body. Thus, the compounds set forth herein provide for a novel form of dietary supplement with capsaicin.

The ester derivatives of capsaicin of the present invention would have significant utility over capsaicin and existing derivatives currently described in the patent and scientific literature. In particular, in view of their high lipophilicity, non-irritation to the stomach, significantly less burning sensation at the site of application and stability, these new derivatives would be more bioavailable when administered orally compared to capsaicin. In addition, because of their stability and non-toxic nature, these agents can be made more readily available to the general public. The inventors have surprisingly and unexpectedly discovered that the ester derivatives of capsaicin utility as a oral dietary supplement for humans. These compounds thus provide for a novel form of supplement wherein capsaicin is believed to be of benefit, including but not limited to, neuropathic pain, chronic pain, headache, arthritis, inflammation, gastric problem, cancer, weight-loss, atherosclerosis, lowering blood cholesterol and blood pressure, weight control and diabetes.

The present invention generally pertains to dietary supplemental compositions containing esterified capsaicinoids, e.g., as described below by formula (I). The term "ester derivatives of capsaicin" or "ester of capsaicin" in the present invention refers to the acylated derivatives of capsaicin and is denoted by the formula I below (e.g., see Figure 3). These derivatives have a higher lipophilicity, lipid solubility and less irritation to the skin than the parent compound, and hence are better able to be incorporated into certain pharmaceutical formulations, including cream and ointment pharmaceutical formulations. Esterified capsaicinoids may be described by the formula:

$$R\text{—}CO\text{—}O_1CAP \qquad (I)$$

wherein CAP refers to a capsaicinoid and $O_1CAP$ refers to an oxygen present in an alcohol group of a corresponding non-esterified capsaicinoid. Various esterified capsaicinoids are described in US 2008/0020996 and U.S. Pat. No. 4,493,848 and U.S. Pat. No. 4,564,633, which are incorporated by reference in its entirety, and may be used with the present invention. Once administered to a subject, the esterified capsaicinoid may be enzymatically converted to the corresponding capsaicinoid once administered to a subject.

In formula I, R is selected from $C_{1-22}$ alkyl, $C_{6-22}$ aryl, $C_{1-22}$ alkylene, $C_{1-22}$ alkenyl, $C_{1-22}$ alkynyl and/or $C_{1-22}$ arylene. In various embodiments, the alkyl, alkylene, alkenyl, alkynyl and/or arylene may be $C_{1-18}$, $C_{1-12}$, or $C_{1-6}$. The aryl may be $C \leq 22$, $C \leq 18$, $C \leq 12$, or $C=6$. The alkyl, aryl and/or alkylene groups may be substituted or unsubstituted, branched or straight chains. In addition, R may contain heteroatoms and may be straight chained or branched.

The compounds of Formula I are esters of capsaicin and its analogues. However, information in the literature does not disclose or indicate the esters of capsaicin have any utility as pro-drug forms suitable for oral delivery for using as dietary supplement.

The present invention may further understood by the following numbered sentences below:

1. An improved nutraceutical or dietary supplemental composition, wherein the improvement comprises the inclusion of an esterified capsaicinoid in the composition, wherein the esterified capsaicinoid has the structure:

$$R\text{—}CO\text{—}O_1CAP \qquad (I)$$

wherein CAP refers to a capsaicinoid and $O_1CAP$ refers to an oxygen present in an alcohol group of a corresponding non-esterified capsaicinoid, wherein R is selected from the group consisting of $C_{1-22}$ alkyl, $C_{6-22}$ aryl, $C_{1-22}$ alkylene, $C_{1-22}$ alkenyl, $C_{1-22}$ alkynyl and $C_{1-22}$ arylene.

2. The composition of sentence 1, wherein R is selected from the group consisting of methyl, ethyl, propyl, butyl, hexyl, heptyl, octyl, dodecyl, 1-pentadecyl, 1-heptadecyl, 1-hexadecyl, 1-octadecyl, isopropyl, sec-butyl, t-butyl, 2-methylbutyl, 2-pentyl, 3-pentyl, cyclopropyl, cyclobutyl, cyclopentyl and cyclohexyl, vinyl (ethenyl), 1-propenyl, i-butenyl, pentenyl, hexenyl, n-decenyl, —CH2-CH2-COOH and c-pentenyl.

3. The composition of sentence 1, wherein said CAP is selected from the capsaicin, civamide, homocapsaicin, nordihydrocapsaicin, dihydrocapsaicin, homodihydrocapsaicin, n-vanillyloctanamide, nonivamide and n-vanillyldecanamide.

4. The composition of sentence 1, wherein said esterified capsaicinoid is capsaicin palmitate (palmitoyl capsaicin) or capsaicin stearate (stearoyl capsaicin).

5. The composition of sentence 1, wherein said composition is formulated for oral administration.

6. The composition of sentence 1, wherein said composition comprises from about 5 to about 25 mg of said esterified capsaicinoid.

7. The composition of sentence 1, wherein said composition comprises one or more additional nutraceutical or dietary supplement agents.

8. The composition of sentence 5, wherein said composition further comprises one or more antioxidants.

9. The composition of sentence 8, wherein the antioxidant is selected from the group consisting of ascorbic acid, sodium ascorbate, ascorbyl palmitate, sodium bisulfite, sodium metabisulfate, curcumin, curcumin derivatives, ursolic acid, resveratrol, resveratrol derivatives, alpha-lipoic acid and monothioglycerol.

10. The composition of sentence 1, wherein said composition further comprises one or more acceptable preservatives or buffering agents.

11. The composition of sentence 10, wherein the composition comprises a buffering agent, wherein the buffering agent is selected from the group consisting of monobasic and dibasic sodium phosphate, sodium benzoate, potassium benzoate, sodium citrate, sodium acetate and sodium tartrate.

12. The dietary supplemental composition of sentence 10, wherein the wherein the composition comprises a preservative, wherein the preservative is methylparaben, methylparaben sodium, propylparaben, propylparaben sodium, benzalkonium chloride or benzthonium chloride.

13. The dietary supplemental composition of sentence 5, wherein the composition comprises one or more acceptable polysaccharides.

14. The dietary supplemental composition of sentence 13, wherein the polysaccharide is dextran sulfate, pectin, modified pectin, insoluble 1,3-β-D glucan, micronized 1,3-β-D glucan, soluble 1,3-β-D glucan, phosphorylated 1,3-β-D glucan, aminated 1,3-β-D glucan and carboxymethylated 1,3-β-D glucan, sulfated 1,3-β-D glucan, insoluble 1,3/1,6-β-D glucan, micronized 1,3/1,6-β-D glucan, soluble 1,3/1,6-β-D glucan, phosphorylated 1,3/1,6-β-D glucan, aminated 1,3/1,6-β-D glucan and carboxymethylated 1,3/1,6-β-D glucan or sulfated 1,3/1,6-β-D glucan.

15. The dietary supplemental composition of sentence 5, wherein the dietary supplement composition comprises from 0.025% to 20% by weight of the esterified capsaicinoid.

16. The dietary supplemental composition of sentence 15, wherein the dietary supplement composition comprises from 0.05% to 20% by weight of the of the esterified capsaicinoid.

17. The dietary supplemental composition of sentence 15, wherein the dietary supplement composition comprises from 0.05% to 10% by weight of the of the esterified capsaicinoid.

18. A method for treating a pathological or disease condition in a human comprising administering to said human a nutraceutical or dietary supplemental composition of sentences 1-17.

19. The method of sentence 18, wherein the pathological or disease condition is selected from the group consisting of post-herpetic neuralgia, diabetic neuropathy, postmastectomy pain syndrome, oral neuropathic pain, trigeminal neuralgia, temperomandibular joint disorders, cluster headache, osteoarthritis, a dermatological or cutaneous disease, chronic pain, arthritis, inflammation, gastric problem, cancer, atherosclerosis, obesity and diabetes.

20. The method of sentence 18, wherein said composition is administered to promote weight-loss, lower blood cholesterol, lower blood pressure, or alter energy metabolism.

21. The method of sentence 20, wherein the said composition is administered to promote weight-loss or lower blood cholesterol.

22. The method of sentence 21, wherein the method further comprises administering from about 10 mg/day to about 25 mg/day of said esterified capsaicinoid to said human.

23. The method of sentence 22, wherein the method further comprises administering from about 15 mg/day to about 20 mg/day of said esterified capsaicinoid to said human.

24. The method of sentence 21, wherein said esterified capsaicinoid is capsaicin palmitate (palmitoyl capsaicin) or capsaicin stearate (stearoyl capsaicin).

25. A method of improving a dietary supplement or nutraceutical composition, wherein the improvement comprises the inclusion of an esterified capsaicinoid of sentence 1.

26. The method of sentence 25, wherein the composition comprises an amount of the esterified capsaicinoid sufficient to lower cholesterol in a human.

27. The method of sentence 25, wherein the composition comprises an amount of the esterified capsaicinoid sufficient to reduce the body weight or treat obesity in a human.

28. The method of sentence 25, wherein said esterified capsaicinoid is capsaicin palmitate (palmitoyl capsaicin) or capsaicin stearate (stearoyl capsaicin).

29. The method of sentence 25, wherein the composition comprises from about 5 to about 40 mg of the esterified capsaicinoid.

30. The method of sentence 29, wherein the composition comprises from about 10 to about 25 mg of the esterified capsaicinoid.

31. The method of sentence 30, wherein the composition comprises from about 15 to about 20 mg of the esterified capsaicinoid.

32. The method of sentence 25, wherein the method further comprises administering said improved dietary supplement or nutraceutical composition to a human to promote a beneficial physiological response or to treat a disease.

33. The method of sentence 32, wherein from about 10 mg/day to about 25 mg/day of said esterified capsaicinoid is administered to said human.

34. The method of sentence 33, wherein said composition is administered to said human to promote weight loss, help prevent obesity, or decrease cholesterol.

35. The method of sentence 34, wherein said esterified capsaicinoid is capsaicin palmitate (palmitoyl capsaicin) or capsaicin stearate (stearoyl capsaicin).

36. The method of sentence 25, wherein the composition further comprises one or more of an antioxidant, a vitamin, a buffering agent, a preservative, or a polysaccharide.

37. The method of sentence 25, wherein the composition is formulated for oral administration.

38. The method of sentence 37, wherein the composition is a tablet or capsule.

The present invention also generally pertains to dietary supplemental compositions comprising one or more of the compounds set forth above.

Accordingly, one aspect of the present invention is to disclose the esters of capsaicin for oral consumption as a dietary supplement. Preferably, the compositions useful in the method may be orally consumed to the human in need of such dietary supplement.

"Nutraceutical," as used herein, refers to a composition comprising extracts of foods that may have a medicinal or therapeutic effect on human health. A nutraceutical composition of the present invention may be comprised in an oral formulation such as a capsule, tablet, or powder in a prescribed dose. In various embodiments, nutraceutical compositions of the present invention can be used to achieve a physiological benefit or provide protection against a chronic disease.

"Dietary supplement," as used herein, refers to a composition which comprises a dietary substance for use by people to supplement the diet by increasing the total dietary intake. In various embodiments, a dietary supplement may be a dietary supplement as defined under the Dietary Supplement Health and Education Act of 1994 (DSHEA). The DSHEA requires that the dietary supplement is as a product that is intended to supplement the diet and contains at least one of the following: a vitamin, a mineral, an herb or other botanical (excluding tobacco), an amino acid, a dietary substance for use by people to supplement the diet by increasing the total dietary intake, or a concentrate, metabolite, constituent, extract, or combination of any of the above. Furthermore, DSHEA requires that the dietary supplement must also be intended for ingestion in pill, capsule, tablet, powder or liquid form, not be represented for use as a conventional food or as the sole item of a meal or diet, and must be labeled as a "dietary supplement."

The use of the esters of the present invention reduces the occurrence of stomach irritation and burning unlike the free capsaicin. In accordance with the method according to this invention, regular use of the esters of capsaicin is meant to mean consumption of the esters of capsaicin orally at least once a day as a supplement.

The dietary compositions of the present invention can additionally include one or more acceptable excipients. One of ordinary skill in the art would be familiar with acceptable excipients. For example, the acceptable excipient may be a water soluble sugar, such as mannitol, sorbitol, fructose, glucose, lactose, and sucrose.

The dietary compositions of the present invention may further comprise one or more acceptable antioxidants. Any acceptable antioxidant known to those of ordinary skill in the art is contemplated for inclusion in the present dietary compositions. For example, the acceptable antioxidant may be selected from the group consisting of ascorbic acid, sodium ascorbate, sodium bisulfate, sodium metabisulfate and monothio glycerol.

The dietary compositions of the present invention may further comprise one or more acceptable preservatives. Any acceptable preservative known to those of ordinary skill in the art is contemplated for inclusion in the present dietary compositions. Examples of such preservatives include methylparaben, methylparaben sodium, propylparaben, propylparaben sodium, benzalkonium chloride, and benzthonium chloride.

The dietary compositions of the present invention may further comprise one or more acceptable buffering agents. Any acceptable buffering agent known to those of ordinary skill in the art is contemplated for inclusion in the present dietary compositions. Examples of such buffering agents include of monobasic sodium phosphate, dibasic sodium phosphate, sodium benzoate, potassium benzoate, sodium citrate, sodium acetate, and sodium tartrate.

The dietary compositions of the present invention can include any concentration of a compound of the present invention. For example, the concentration of compound may be 0.1 mg/dose to 200 mg/dose or greater. In certain particular embodiments, the concentration of compound is 1 mg/dose to 100 mg/dose. In still further embodiments, the concentration of compound is 5 mg/dose to 50 mg/dose.

In some embodiments of the present invention, the composition includes more than one of the novel compounds set forth above. In other embodiments of the present invention, the composition includes one or more secondary supplement agents directed to a disease or health-related condition, as discussed below.

The present invention also generally pertains to methods of treating or preventing a pathological condition in a subject, comprising providing an effective amount of any of the compositions set forth above, and administering the composition to the subject. The subject can be any subject, such as a mammal or avian species. In certain particular embodiments, the mammal is a human. The human may be an individual affected by or at risk of developing a disease or condition amenable to dietary supplement with capsaicin. For example, the compositions can be used as supplement for, but not limited to, neuropathic pain, chronic pain, headache, arthritis, inflammation, gastric problem, cancer, weight-loss, atherosclerosis, lowering blood cholesterol and blood pressure, weight control and diabetes.

The composition of the present invention may be administered to the subject by any method known to those of ordinary skill in the art. For example, the method of administering the composition to the subject may include oral, topical, nasal, inhalational, rectal, or vaginal. Methods of administration are discussed in greater detail in the specification below.

In certain embodiments of the methods of the present invention, the method involves administering to the subject an effective amount of a secondary agent. The secondary agent can be any agent known or suspected to be of benefit in the treatment or prevention of a disease or health-related condition in a subject. For example, in some embodiments, the secondary agent is a secondary pain relieving agent. Secondary pain relieving agents, which include morphine, are well-known to those of ordinary skill in the art. Examples of such agents include aspirin, acetaminophen (Tylenol) or other aspirin-like drugs called nonsteroidal anti-inflammatory drugs (NSAIDs), weak narcotics such as codeine (Tylenol with codeine), hydrocodone (Vicodin or Lortab), Percocet, Percodan or propoxyphene (Darvon), strong opioids such as morphine, Demerol, Dilaudid, fentanyl (duragesic patches) and methadone.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

The present invention provides improved nutraceutical and/or dietary supplemental compositions comprising an esterified capsaicinoid. The present invention is based on the inventors' discovery of certain compositions containing esters of capsaicinoids are highly lipophilic, non-irritating, and thus allow higher concentrations for improved bioavailability following administration in a cream or oral formulations. The compositions of the present invention include esters of capsaicin. These compounds are suitable by any route of administration, but are particularly suited for oral or topical administration in view of their lipid solubility. These dietary supplemental compositions thus provide for a novel form of dietary supplement of any disease or condition wherein capsaicin is believed to be of benefit including, e.g., neuropathic pain, chronic pain, headache, arthritis, inflammation, gastric problem, cancer, weight-loss, atherosclerosis, lowering blood cholesterol and blood pressure, weight control and diabetes.

A. Esterified Capsaicinoids

Capsaicinoids are well known in the art and can be found in various plants, such as hot chili peppers. The term "capsaicinoid" or "capsaicins" as used herein is intended to encompass not only the compound capsaicin, but also homocapsaicin, nordihydrocapsaicin, dihydrocapsaicin, homodihydrocapsaicin or any compounded mixture thereof. The chemical structures of various capsaicinoids are shown below:

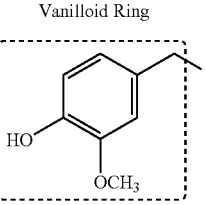

| Capsaicinoid Analogue | R-Group Composition |
|---|---|
| Capsaicin | $CO(CH_2)_4(CH)_2CH(CH_3)_2$ |
| Homocapsaicin | $CO(CH_2)_5(CH)_2CH(CH_3)_2$ |
| Nordihydrocapsaicin | $CO(CH_2)_5CH(CH_3)_2$ |
| Dihydrocapsaicin | $CO(CH_2)_6CH(CH_3)_2$ |
| Homodihydrocapsaicin | $CO(CH_2)_7CH(CH_3)_2$ |
| n-Vanillyloctanamide | $CO(CH_2)_6CH_3$ |
| Nonivamide | $CO(CH_2)_7CH_3$ |
| n-Vanillyldecanamide | $CO(CH_2)_8CH_3$ |

Examples of the chemical structures of capsaicin esters which may be used according to the present invention are shown below:

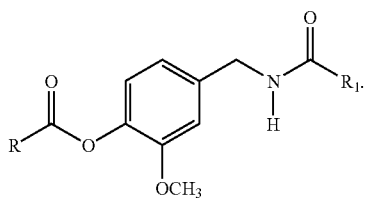

1. Capsaicin Ester $R1=(CH_2)_4(CH)_2CH(CH_3)_2$
2. Homocapsaicin Ester $R1=(CH_2)_5(CH)_2CH(CH_3)_2$
3. Nordihydrocapsaicin Ester $R1=(CH_2)_5CH(CH_3)_2$
4. Dihydrocapsaicin Ester $R1=(CH_2)_6CH(CH_3)_2$
5. Homodihydrocapsaicin Ester $R1=(CH_2)_7CH(CH_3)_2$
6. n-Vanillyloctanamide Ester $R1=(CH_2)_6CH_3$
7. Nonivamide Ester $R1=(CH_2)_7CH_3$
8. n-Vanillyldecanamide Ester $R1=(CH_2)_8CH_3$ It is to be understood that this invention is not limited to particular drugs or drug delivery systems, as such may vary. It is also to be understood that the terminology used herein is for the purpose of describing particular embodiments only, and is not intended to be limiting.

It must be noted that, as used in this specification, the singular forms "a," "an" and "the" include plural referents unless the context clearly dictates otherwise. Thus, for example, reference to "an active agent" includes a combination of two or more active agents, and the like. In describing the present invention, the following terminology will be used in accordance with the definitions set out below.

As used herein in the claim(s), when used in conjunction with the word "comprising", the words "a" or "an" may mean one or more than one. As used herein "another" may mean at least a second or more.

The terms "active agent," "dietary supplement" and "pharmacologically active agent" are used interchangeably herein to refer to a chemical material or compound which, when administered to an organism (human or animal) induces a desired pharmacologic effect. Included are derivatives and analogs of those compounds or classes of compounds specifically mentioned which also induce the desired pharmacologic effect.

The term "topical administration" is used in its conventional sense to mean delivery of a topical dietary supplement, or pharmacologically active agent to the skin or mucosa.

"Carriers" or "vehicles" as used herein refer to carrier materials suitable for drug administration. Carriers and vehicles useful herein include any such materials known in the art, e.g., any liquid, gel, solvent, liquid diluent, solubilizer, or the like, which is nontoxic and which does not interact with other components of the composition in a deleterious manner.

By an "effective" amount of a dietary supplement or pharmacologically active agent is meant a nontoxic but sufficient amount of the dietary supplement or agent to provide the desired effect.

The term "capsaicin or capsaicins" as used herein is intended to encompass not only the compound capsaicin, but also homocapsaicin, nordihydrocapsaicin, dihydrocapsaicin, homodihydrocapsaicin or any compounded mixture thereof.

The term "dietary supplement" or "supplement" is defined under the Dietary Supplement Health and Education Act of 1994 (DSHEA) as a product that is intended to supplement the diet and contains any of the following dietary ingredients: a vitamin, a mineral, an herb or other botanical (excluding tobacco), an amino acid, a dietary substance for use by people to supplement the diet by increasing the total dietary intake, or a concentrate, metabolite, constituent, extract, or combination of any of the above. Furthermore, it must also conform to the following criteria: a) intended for ingestion in pill, capsule, tablet, powder or liquid form; b) not represented for use as a conventional food or as the sole item of a meal or diet; and c) labeled as a "dietary supplement".

The present invention provides for certain novel dietary supplement compositions containing ester derivatives of capsaicin that are highly lipophilic. The ester of capsaicin set forth herein is enzymatically cleaved to the parent compound. Thus, the dietary compositions set forth herein provide for a novel form of supplement of diseases or pathological conditions amendable to treatment with capsaicin.

The ester derivatives of capsaicin of the present invention would have significant utility over capsaicin or and existing derivatives currently described in the patent and scientific literature. In particular, in view of their high lipophilicity, non-irritation to the skin and stomach, significantly less burning sensation at the site of application and stability, these derivatives would be more bioavailable when administered topically or orally compared to capsaicin. In addition, because of their stability and non-toxic nature, these agents can be made more readily available to the general public.

The inventors have surprisingly and unexpectedly discovered that the ester derivatives of capsaicin has therapeutic utility as a dietary supplement in treating various pathological conditions in humans. These compositions thus provide for a novel form of therapy of any disease or condition wherein capsaicin is believed to be of benefit, including but not limited to, post-herpetic neuralgia, shingles (herpes zoster), diabetic neuropathy, postmastectomy pain syndrome, oral neuropathic pain, trigeminal neuralgia, temperomandibular joint disorders, pruritus, cluster headache, osteoarthritis, arthritis pain, rhinopathy, oral mucositis, cutaneous allergy, detrusor hyperreflexia, loin pain/hematuria syndrome, neck pain, amputation stump pain, reflex sympathetic dystrophy, pain due to skin tumor, inflammation, gastric problem, cancer, weight-loss, atherosclerosis, lowering blood cholesterol and blood pressure, weight control and diabetes.

The present invention generally pertains to dietary supplemental compositions containing a compound of formula (I):

$$R-CO-O_1CAP \quad (I)$$

wherein CAP refers to a capsaicinoid and O₁CAP refers to an oxygen present in an alcohol group of a corresponding non-esterified capsaicinoid. Various esterified capsaicinoids are described in US 2008/0020996 and U.S. Pat. No. 4,493,848 and U.S. Pat. No. 4,564,633, which are incorporated by reference in its entirety, and may be used with the present invention. Once administered to a subject, the esterified capsaicinoid may be enzymatically converted to the corresponding capsaicinoid once administered to a subject.

In formula I, R is selected from $C_{1-22}$ alkyl, $C_{6-22}$ aryl, $C_{1-22}$ alkylene, $C_{1-22}$ alkenyl, $C_{1-22}$ alkynyl and/or $C_{1-22}$ arylene. In various embodiments, the alkyl, alkylene, alkenyl, alkynyl and/or arylene may be $C_{1-18}$, $C_{1-12}$, or $C_{1-6}$. The aryl may be $C \leq 22$, $C \leq 18$, $C \leq 12$, or $C=6$. The alkyl, aryl and/or alkylene groups may be substituted or unsubstituted, branched or straight chains. In addition, R may contain heteroatoms and may be straight chained or branched.

Examples of suitable straight-chain alkyl groups in formula I include methyl, ethyl, propyl, butyl, hexyl, heptyl, octyl, dodecyl, 1-pentadecyl, 1-heptadecyl and the like groups.

Examples of suitable branched chain alkyl groups in formula I include isopropyl, sec-butyl, t-butyl, 2-methylbutyl, 2-pentyl, 3-pentyl and the like groups.

Examples of suitable cyclic alkyl groups in formula I include cyclopropyl, cyclobutyl, cyclopentyl and cyclohexyl groups.

Examples of suitable "alkenyl" groups in formula I include vinyl (ethenyl), 1-propenyl, i-butenyl, pentenyl, hexenyl, n-decenyl and c-pentenyl and the like.

The groups may be substituted, generally with 1 or 2 substituents, wherein the substituents are independently selected from halo, hydroxy, alkoxy, amino, mono- and dialkylamino, nitro, carboxyl, alkoxycarbonyl, and cyano groups.

By the expression "phenalkyl groups wherein the alkyl moiety contains 1 to 3 or more carbon atoms" is meant benzyl, phenethyl and phenylpropyl groups wherein the phenyl moiety may be substituted. When substituted, the phenyl moiety of the phenalkyl group may contain independently from 1 to 3 or more alkyl, hydroxy, alkoxy, halo, amino, mono- and dialkylamino, nitro, carboxyl, alkoxycarbonyl and cyano groups.

Examples of suitable "heteroaryl" in formula I are pyridinyl, thienyl or imidazolyl.

As noted herein, the expression "halo" is meant in the conventional sense to include F, Cl, Br, and I.

Among the compounds represented by the general Formula I, preferred compounds are such in which R is one of the following groups: methyl, ethyl, propyl, butyl, pentyl, hexyl, 1-pentadecyl, 1-heptadecyl, isobutyl, methoxyethyl, ethoxyethyl, benzyl and nicotinyl.

A non-limiting list of capsaicin which may be used in the present invention include capsaicin, homocapsaicin, nordihydrocapsaicin, dihydrocapsaicin, homodihydrocapsaicin or any compounded mixture thereof. Capsaicin palmitate is an ester of capsaicin which may be used with the present invention.

For oral administration, the preferred ester is the palmitate esters of capsaicins. These esters result in less irritation and burning sensation to the stomach, as compared to capsaicin. Without wishing to be bound by any theory, pain relief is achieved via binding to the VR1 receptors and the depletion of substance P.

For the groups below, the following parenthetical subscripts further define the groups as follows: "(Cn)" defines the exact number (n) of carbon atoms in the group; "(C≤n)" defines the maximum number (n) of carbon atoms that can be in the group; (Cn-n') defines both the minimum (n) and maximum number (n') of carbon atoms in the group. For example, "alkoxy$_{(C \leq 10)}$" designates those alkoxy groups having from 1 to 10 carbon atoms (e.g., 1, 2, 3, 4, 5, 6, 7, 8, 9, or 10, or any range derivable therein (e.g., 3-10 carbon atoms)). Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3-10 carbon atoms)).

The term "alkyl" when used without the "substituted" modifier refers to a non-aromatic monovalent group, having a saturated carbon atom as the point of attachment, a linear or branched, cyclo, cyclic or acyclic structure, no carbon-carbon double or triple bonds, and no atoms other than carbon and hydrogen. The groups, —CH₃ (Me), —CH₂CH₃ (Et), —CH₂CH₂CH₃ (n-Pr), —CH(CH₃)₂ (iso-Pr), —CH(CH₂)₂ (cyclopropyl), —CH₂CH₂CH₂CH₃ (n-Bu), —CH(CH₃)CH₂CH₃ (sec-butyl), —CH₂CH(CH₃)₂ (iso-butyl), —C(CH₃)₃ (tert-butyl), —CH₂C(CH₃)₃ (neo-pentyl), cyclobutyl, cyclopentyl, cyclohexyl, and cyclohexylmethyl are non-limiting examples of alkyl groups. The term "substituted alkyl" refers to a non-aromatic monovalent group, having a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH₂OH, —CH₂Cl, —CH₂Br, —CH₂SH, —CF₃, —CH₂CN, —CH₂C(O)H, —CH₂C(O)OH, —CH₂C(O)OCH₃, —CH₂C(O)NH₂, —CH₂C(O)NHCH₃, —CH₂C(O)CH₃, —CH₂OCH₃, —CH₂OCH₂CF₃, —CH₂OC(O)CH₃, —CH₂NH₂, —CH₂NHCH₃, —CH₂N(CH₃)₂, —CH₂CH₂Cl, —CH₂CH₂OH, —CH₂CF₃, —CH₂CH₂OC(O)CH₃, —CH₂CH₂NHCO₂C(CH₃)₃, and —CH₂Si(CH₃)₃.

The term "alkenyl" when used without the "substituted" modifier refers to a monovalent group, having a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH═CH₂ (vinyl), —CH═CHCH₃, —CH═CHCH₂CH₃, —CH₂CH═CH₂ (allyl), —CH₂CH═CHCH₃, and —CH═CH—C₆H₅. The term "substituted alkenyl" refers to a monovalent group, having a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH═CHF, —CH═CHCl and —CH═CHBr, are non-limiting examples of substituted alkenyl groups.

The term "alkynyl" when used without the "substituted" modifier refers to a monovalent group, having a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH₃, —C≡CC₆H₅ and —CH₂C≡CCH₃, are non-limiting examples of alkynyl groups. The term "substituted alkynyl" refers to a monovalent group, having a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH₃)₃, is a non-limiting example of a substituted alkynyl group.

The term "aryl" when used without the "substituted" modifier refers to a monovalent group, having a aromatic carbon atom as the point of attachment, said carbon atom forming part of a six-membered aromatic ring structure wherein the ring atoms are all carbon, and wherein the monovalent group consists of no atoms other than carbon and hydrogen. Non-limiting examples of aryl groups include phenyl (Ph), methylphenyl, (dimethyl)phenyl, —$C_6H_4CH_2CH_3$ (ethylphenyl), —$C_6H_4CH_2CH_2CH_3$ (propylphenyl), —$C_6H_4CH(CH_3)_2$, —$C_6H_4CH(CH_2)_2$, —$C_6H_3(CH_3)CH_2CH_3$ (methylethylphenyl), —$C_6H_4CH=CH_2$ (vinylphenyl), —$C_6H_4CH=CHCH_3$, —$C_6H_4C\equiv CH$, —$C_6H_4C\equiv CCH_3$, naphthyl, and the monovalent group derived from biphenyl. The term "substituted aryl" refers to a monovalent group, having a aromatic carbon atom as the point of attachment, said carbon atom forming part of a six-membered aromatic ring structure wherein the ring atoms are all carbon, and wherein the monovalent group further has at least one atom independently selected from the group consisting of N, O, F, Cl, Br, I, Si, P, and S, Non-limiting examples of substituted aryl groups include the groups: —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OC(O)CH_3$, —$C_6H_4NH_2$, —$C_6H_4NHCH_3$, —$C_6H_4N(CH_3)_2$, —$C_6H_4CH_2OH$, —$C_6H_4CH_2OC(O)CH_3$, —$C_6H_4CH_2NH_2$, —$C_6H_4CF_3$, —$C_6H_4CN$, —$C_6H_4CHO$, —$C_6H_4CHO$, —$C_6H_4C(O)CH_3$, —$C_6H_4C(O)C_6H_5$, —$C_6H_4CO_2H$, —$C_6H_4CO_2CH_3$, —$C_6H_4CONH_2$, —$C_6H_4CONHCH_3$, and —$C_6H_4CON(CH_3)_2$.

An "isomer" of a first compound is a separate compound in which each molecule contains the same constituent atoms as the first compound, but where the configuration of those atoms in three dimensions differs.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2] oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, Selection and Use* (P. H. Stahl & C. G. Wermuth eds., Verlag Helvetica Chimica Acta, 2002), which is incorporated herein by reference.

The compounds of Formula I are esters of capsaicin and its analogues. However, information in the literature does not disclose or indicate the esters of capsaicin have any utility as pro-drug forms suitable for oral delivery for using as dietary supplement for treating, including but not limited to, post-herpetic neuralgia, shingles (herpes zoster), diabetic neuropathy, postmastectomy pain syndrome, oral neuropathic pain, trigeminal neuralgia, temperomandibular joint disorders, pruritus, cluster headache, osteoarthritis, arthritis pain, rhinopathy, oral mucositis, cutaneous allergy, detrusor hyperreflexia, loin pain/hematuria syndrome, neck pain, amputation stump pain, reflex sympathetic dystrophy, pain due to skin tumor, inflammation, gastric problem, cancer, weight-loss, atherosclerosis, lowering blood cholesterol and blood pressure, weight control and diabetes.

B. Methods of Synthesis

The compounds used in the present invention can be prepared by any method known to those of ordinary skill in the art. Various methods have been described in the) literature pertaining to the synthesis of a number of esters of carboxylic acids and phenols (March's Advanced Organic Chemistry: Reactions, Mechanisms, and Structure, 5th Edition, by Michael B. Smith and Jerry March, John Wiley and Sons, Inc, 2001).

One method that has been utilized for efficient preparation of the ester of capsaicin of the present invention is through dissolution of the compound in methylene dichloride. Since capsaicin USP contains >95% of capsaicins, to this solution slightly in excess of 1.1 mole equivalent of anhydrous triethylamine is added with stirring at room temperature. To this solution slightly in excess of 1 mole equivalent of an acid chloride is added with stirring while keeping the temperature around 25° C. After that, the solution was refluxed for 2-5 hours and stirred for 12-17 hours at room temperature. The reaction mixture was then washed with equal amount of water three to four times to remove the unreacted amine and its salt in a separating funnel. The organic phase was washed 3-4 times with dilute hydrochloric acid solution in a separating funnel to remove any amine present in the organic solution. The reaction mixture was then washed with equal amount of 10% sodium carbonate solution three to four times to remove the unreacted acid and salts in a separating funnel. The reaction mixture was then washed with equal amount of water three to four times in a separating funnel. The organic phase was dried with anhydrous sodium sulfate overnight and the methylene dichloride was removed in a rotary evaporator under vacuum. The resultant oily or waxy material is called the ester capsaicin as all of the phenols present capsaicin is converted into the corresponding ester.

C. Dietary Supplement Compositions

Certain embodiments of the present invention pertain to dietary supplement compositions comprising the esters of capsaicins set forth herein. In certain embodiments, one or more esterified capsaicinoid of the present invention is comprised in a nutraceutical composition.

The phrases "dietary supplement," or "pharmacologically acceptable agent" refer to molecular entities and compositions that do not produce an unacceptably adverse, allergic or other untoward reaction when administered to an animal, or human, as appropriate. As used herein, "dietary supplement" includes any and all herbs, extracts, dispersion media, coatings, antibacterial and antifungal agents, isotonic and absorption delaying agents and the like. The use of such media and agents for dietary supplements is well known in the art. Except insofar as any conventional media or agent is incompatible with the active ingredients, its use in the dietary compositions is contemplated. Supplementary active ingredients to treat the disease of interest, such as other anti-inflammatory agents, can also be incorporated into the compositions.

Dietary supplement compositions of the present invention will include an effective amount of one or more of the ester derivatives of capsaicin set forth herein that are clinically determined to be useful in the treatment of the particular disease or pathological conditions under consideration. One of ordinary skill in the art would be familiar with what type of dosage is required for treatment of the particular pathological condition that is present in the subject. No undue experimentation would be involved. When used for therapy, the compositions of the present invention are administered to subjects in therapeutically effective amounts. For example, an effective amount of the ester of capsaicin in a patient with diabetic neuropathy may be an amount that promotes the healing of the pain associated with the neuropathy. The dose will depend on the nature of the disease, the subject, the subject's history, and other factors. Preparation of such compositions is discussed in other parts of this specification.

As discussed above, the derivatives of capsaicin set forth herein have greater lipophilicity and significantly less irritation to the stomach when taken orally than capsaicin. One advantage of these esters is that they can be incorporated into a capsule, tablet or pill form at a higher percentage by weight as compared to capsaicin. Another advantage is that these compositions have a very low toxicity and irritation to the stomach as compared to formulations of capsaicin.

The compositions of the capsaicin derivatives of the present invention can be delivered by any method known to those of ordinary skill in the art. For example, the dietary supplemental compositions can be delivered by topical or oral delivery routes.

Compositions employing the esters of capsaicin set forth herein will contain a biologically effective amount of the derivative. As used herein a biologically effective amount of a compound or composition refers to an amount effective to alter, modulate or reduce disease conditions. One of ordinary skill in the art would be familiar with methods of determining a biologically effective amount of a therapeutic agent. For example, a biologically effective amount may be about 0.1 mg/kg to about 10 mg/kg or greater.

The dietary supplement combination of esters of capsaicin of the present invention may be administered alone or in combination with one or more additional esters of the present invention. In other embodiments, the dietary supplement combination of ester of capsaicin is administered in combination with one or more secondary forms of therapy directed to the disease or condition to be treated. These are discussed in greater detail below. Additional pharmaceutical compounds or dietary supplemental compounds may be administered in the same dietary supplemental composition, or in a separate dosage form, such as in a separate oral, intramuscular, or intravenous dosage forms taken at the same time.

The dietary supplement agents of the present invention may be supplied in any form known to those of ordinary skill in the art. For example, the dietary supplement agent may be supplied as a liquid or as a solution. The dietary supplement compositions may contain a preservative to prevent the growth of microorganisms. It must be chemically and physically stable under the conditions of manufacture and storage and must be preserved against the contaminating action of microorganisms, such as bacteria and fungi. The prevention of the action of microorganisms can be brought about by various antibacterial and antifungal agents, for example, parabens, chlorobutanol, phenol, sorbic acid, thimerosal, and the like.

The formulations according to the invention having been described herein may influence the ordinarily skilled artesian to make similar formulations using components that will be known in the art, without departing from the invention which is claimed herein.

The dietary supplement formulations of the esters of capsaicinoids according to the present invention offer several advantages over the existing formulations. They can be orally administered as a dietary supplement and relatively high concentrations of the esters of capsaicin can be loaded into humans with high bioavailability. Thus the frequency of dosage can be reduced. Thus within the spirit, the invention is related to improved formulations and methods of using the same when administering such formulations to humans. As mentioned herein above a number of excipients may be appropriate for use in the formulation which comprises the composition according to the present invention. The inclusion of excipients and the optimization of their concentration for their characteristics such as for example ease of handling or carrier agents will be understood by those ordinarily skilled in the art not to depart from the spirit of the invention as described herein and claimed herein below.

Following preparation of the dietary supplemental compositions of the present invention, it may be desirable to quantify the amount of the esters of capsaicin and esters of myristoleic acid in the dietary supplemental composition. Methods of measuring concentration of a drug in a composition include numerous techniques that are well-known to those of skill in the art. Selected examples include chromatographic techniques. There are many kinds of chromatography which may be used in the present invention: drug-specific assays, adsorption, partition, ion-exchange and molecular sieve, and many specialized techniques for using them including column, paper, thin-layer chromatography, gas chromatography, and high performance liquid chromatography (HPLC). One of ordinary skill in the art would be familiar with these and other related techniques.

D. Antioxidants

Certain topical formulations of the present invention may also contain one or more antioxidants. Non-limiting examples of antioxidants that can be used with the compositions of the present invention include acetyl cysteine, ascorbic acid, ascorbic acid polypeptide, L-ascorbate (vitamin C), vitamin E, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

E. Pathological Conditions to be Treated or Prevented

As noted in other parts of this specification, there is substantial evidence that capsaicin would be beneficial in the treatment of a wide variety of pathological conditions. The term "treat" or "treatment" means that the symptoms associated with one or more conditions mentioned above are alleviated or reduced in severity or frequency and the term "prevent" means that subsequent occurrences of such symptoms are avoided or that the frequency between such occurrences is prolonged.

A dietary supplement or nutraceutical composition of the present invention may contain, e.g., from about 0.5 mg to about 40 mg, from about 1 mg to about 35 mg, from about 10 mg to about 25 mg, from about 15 mg to about 25 mg, from about 16 mg to about 20 mg, or any range derivable therein of said esterified capsaicinoid. In certain embodiments, the esterified capsaicinoid is capsaicin palmitate (palmitoyl capsaicin) or capsaicin stearate (stearoyl capsaicin).

In various embodiments, from about 0.5 mg/day to about 40 mg/day, from about 1 mg/day to about 35 mg/day, from about 10 mg/day to about 25 mg/day, from about 15 mg/day to about 25 mg/day, from about 16 mg/day to about 20 mg/day, or any range derivable therein of said esterified capsaicinoid is administered to a human patient to treat a disease or promote a beneficial physiological effect. The esterified capsaicinoid, e.g., capsaicin palmitate or capsaicin stearate, may be administered to promote weight-loss, help prevent obesity, and/or decrease cholesterol. For example, as described in further detail below in the examples, from about 10 mg/day to about 25 mg/day or 16 mg/day to about 20 mg/day of capsaicin palmitate may be administered to a human patient to reduce cholesterol.

Conditions amenable to treatment or prevention with capsaicin are specifically detailed for post-herpetic neuralgia (Bernstein et al., 1989; Watson et al., 1993), diabetic neuropathy (Capsaicin Study Group, 1992), postmastectomy pain syndrome (Watson and Evans, 1992; Dini et al., 1993), oral neuropathic pain, trigeminal neuralgia, and temperomandibular joint disorders (Epstein and Marcoe, 1994; Hersh et al., 1994), cluster headache (following intranasal application; Marks et al., 1993; Levy 1995), osteoarthritis (McCarthy and McCarthy, 1992), dermatological and cutaneous conditions (Hautkappe et al., 1998), chronic pain (Fusco 1997), arthritis (Deal 1991), inflammation (Singh 1996), gastric problem (Horowitz 1992; Pimparkar 1972), cancer (Morr 1995; Lee 2001; Jung 2001; Mori 2006), weight-loss (Visudhiphan 1982), atherosclerosis, lowering blood cholesterol (Saito 1999; Sambaiah 1980), lowering blood pressure (Franco-Cereceda 1989; Jansen-Olesen 1996; Wang 1982), increase in energy metabolism (Griffiths 1996; Kawada 1986; Yoshioka 1995; 1999; Lim 1997), obesity (Melnyk 1995; Yoshioka 1998; Lejeune 2003; Gram 2005) and diabetes (Pfeifer 1993; Ahuja 2006; Tolan 2004 & 2001; Domotor 2006).

Examples of pathological conditions responsive to capsaicin therapy include, but are not limited to, post-herpetic neuralgia, shingles (herpes zoster), diabetic neuropathy, post-mastectomy pain syndrome, oral neuropathic pain, trigeminal neuralgia, temperomandibular joint disorders, pruritus, cluster headache, osteoarthritis, arthritis pain, rhinopathy, oral mucositis, cutaneous allergy, detrusor hyperreflexia, loin pain/hematuria syndrome, neck pain, amputation stump pain, reflex sympathetic dystrophy, arthritis, inflammation, gastric problem, cancer, obesity, atherosclerosis, lowering blood cholesterol and blood pressure, weight control and diabetes.

It is expected that the novel dietary supplement composition containing ester derivatives of capsaicin set forth herein would be beneficial in the treatment and prevention of any of the diseases set forth above. One of ordinary skill in the art would be familiar with the many diseases and conditions that would be amenable to treatment with one or more of the ester derivatives of capsaicin set forth herein.

F. Secondary Therapies

Some embodiments of the claimed methods of the present invention involve administering to the subject a secondary form of therapy in addition to one or more of the combination of ester derivatives of capsaicin set forth herein. For example, if the disease is a hyperproliferative disease, such as cancer, the secondary therapy may be a chemotherapeutic agent, radiation therapy, surgical therapy, immunotherapy, gene therapy, or other form of anticancer therapy well-known to those of ordinary skill in the art. If the disease is an inflammatory disease such as arthritis, exemplary secondary forms of therapy include non-steroidal anti-inflammatory agents, steroids and immunosuppressant therapy.

In order to increase the effectiveness of the dietary supplement disclosed herein, it may be desirable to combine the dietary supplement of the present invention with the secondary therapeutic agent. These compositions would be provided in a combined amount effective to provide for a therapeutic response in a subject. One of ordinary skill in the art would be able to determine whether the subject demonstrated a therapeutic response. This process may involve administering the dietary supplement of the present invention and the secondary therapeutic agent to the subject at the same time. This may be achieved by administering a single composition or pharmacological formulation that includes both agents, or by administering two distinct compositions or formulations, at the same time, wherein one composition includes the ester derivative of capsaicin of the present invention and the other includes the secondary agent.

Alternatively, the dietary supplement of the present invention may precede or follow the treatment with the secondary agent by intervals ranging from minutes to weeks. In embodiments where the secondary agent and the ester derivatives of the present invention are separately administered, one would generally ensure that a significant period of time did not expire between the time of each delivery, such that the secondary agent and the therapeutic agent of the present invention would still be able to exert a beneficial effect on the subject. In such instances, it is contemplated that one may administer both modalities within about 24-48 h of each other and, more preferably, within about 12-24 h of each other, and even more preferably within about 30 minute-6 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, the therapeutic agent of the present invention is "A" and the secondary agent, such as chemotherapy, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the compositions of the present invention to a patient will follow general protocols for the administration of therapeutic agents, such as chemotherapy where the disease to be treated is cancer. It is expected that the treatment cycles would be repeated as necessary.

G. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of Butyryl Ester of Capsaicin USP
(Formula I, R=$C_3H_7$)

A mixture of 30.5 gm (~0.1M) of capsaicin USP (HUBEI XIANGXI CHEMICAL INDUSTRY CO., LTD, China), 16.7 ml (0.12M) of anhydrous triethylamine (Spectrum Chemicals) and 200 ml of anhydrous dichloromethane was placed into a 1000 ml 2-neck round bottomed flask. The content was covered with aluminum foil to protect it from light exposure. The flask was fitted with a condenser fitted with a moisture trap on the top and a dropwise addition funnel. The flask was kept at room temperature and 12.8 ml (0.12M) of butyryl chloride was added from the funnel into the mixture slowly with stirring. After the addition, the mixture was refluxed for 3-6 hours and stirred for 10-15 hours at room temperature. The mixture was transferred into a separating funnel and washed successively with 2×500 ml of water, 2×500 ml of dilute hydrochloric acid, 2×500 ml of 10% sodium bicarbonate solution and 3×500 ml of type I water. The organic layer was separated, dried with anhydrous magnesium sulfate and the dichloromethane was removed under vacuum to produce a clear, yellow viscous oil (95% of theoretical).

Example 2

Preparation of Hexanoyl Ester of USP (Formula I, R=$CH_3$—$(CH_2)_4$)

The compound was prepared essentially as described in Example 1, using n-hexanoyl chloride instead of butyryl chloride. The product was recovered as a low melting viscous yellow oil.

Example 3

Preparation of Palmitoyl Ester of Capsaicin USP
(Formula I, R=$CH_3$—$(CH_2)_{14}$)

The compound was prepared essentially as described in Example 1, using n-palmitoyl chloride instead of butyryl chloride. The product was recovered as a waxy yellow solid.

Example 4

Preparation of Capsules Containing Palmitoyl Capsaicin USP

The capsule composition is compounded from the following ingredients given in Table 1.

TABLE 1

The composition for the preparation of capsules.

| Ingredient | Amount I | Amount II |
|---|---|---|
| Palmitoyl-Capsaicin USP | 5.40 parts | 10.8 parts |
| Microcrystalline Cellulose | 88.10 parts | 82.70 parts |
| Ascorbyl palmitate | 20.00 parts | 20.00 parts |
| Silicon dioxide | 2.50 parts | 2.50 parts |
| Magnesium Stearate | 1.50 parts | 1.50 parts |
| Sodium lauryl sulfate | 2.50 parts | 2.50 parts |
| Total | 120.00 parts | 120.00 parts |

PREPARATION I: The palmitoyl-capsaicin USP (Table 1; Amount I) is intensively milled with ten times its weight of microcrystalline cellulose, the milled mixture is admixed with the remaining amount of the microcrystalline cellulose, ascorbyl palmitate sodium lauryl sulfate and silicon dioxide. The mixed powder is again milled and the composition is filled into 120 mg capsule in a conventional capsule loading machine. Each capsule contains 5.40 mg of palmitoyl-capsaicin USP (approximately 40,000 SHU equivalent in each capsule) and is an oral dosage unit composition with effective therapeutic action.

PREPARATION II: The palmitoyl-capsaicin-USP (Table 1; amount II) is intensively milled with five times its weight of microcrystalline cellulose, the milled mixture is admixed with the remaining amount of the microcrystalline cellulose, ascorbyl palmitate, sodium lauryl sulfate and silicon dioxide. The mixed powder is again milled and the composition is filled into 120 mg capsule in a conventional capsule loading machine. Each capsule contains 10.8 mg of palmitoyl-capsaicin USP (approximately 80,000 SHU equivalent in each capsule) and is an oral dosage unit composition with effective therapeutic action.

Example 5

Toxicity Assessment of the Inventive Composition

A 5.4 mg of palmitoyl-capsaicin USP as described in example 4 was administered twice daily to 10 healthy individuals for a two-week period. No individual complained of burning or irritation in the stomach after consuming the capsules.

Example 6

Administration to Young Male with Obesity

A 24 year old white male was given the capsules of formulation 1 above. He habitually maintained a high fat diet and was overweight for his size. He gave the following testimony. "I am a healthy 24 year old male that is not very active usually. After 3-4 weeks of taking 5.4 mg Capsaicin Palmitate capsules two times daily, along with a mixed diet consisting largely of fast food variety meals, I had maintained an average weight, with a fluctuation of 2-3 pounds over and under but always within a few days returning to the average. During this time, I also noticed that fatty, greasy foods were more quickly moved through my digestive system than were more wholesome meals (whole grains, fruit, and/or vegetables) of comparable quantity, noticeable upon bowel movements".

Example 7

Treatment of Diabetic Neuropathy and Reduction of LDL

A 50 year old white male was diagnosed with diabetic neuropathy and he was given capsules of formulation 1 in Example 4. He has provided the following testimony after using the capsules. "I have great pain due to diabetic neuropathy in my legs and feet. I became naturopathic after a long series of intravenous antibiotics. In an effort to ease the pain I have overdosed on aspirin, taken prescribed antidepressants, and even heavy narcotics. All these medicines would only curb the pain enabling me to get a couple hours of sleep a night. I was taking Tramadol and Dextromethorphan for controlling my pain and in addition, I was taking three capsules of Capsaicin palmitate (5.4 mg) every day. Before taking the medication, my doctor told me I was high on cholesterol and my LDL cholesterol was around 190 mg/dl. After six months, I went to see the doctor again and he told me that my cholesterol was at normal level and my LDL cholesterol was round 110 mg/dl. He was very surprised by the result as I was not taking any cholesterol lowering medication and I told him about the capsaicin palmitate".

We claim:

1. A nutraceutical or dietary supplemental composition, comprising one or more esterified capsaicinoids, wherein the esterified capsaicinoid has the structure:

$$R-CO-O_1CAP \quad (I)$$

wherein CAP refers to a capsaicinoid and $O_1CAP$ refers to an oxygen present in an alcohol group of a corresponding non-esterified capsaicinoid, wherein R is selected from the group consisting of $C_{1-22}$ alkyl, $C_{6-22}$ aryl, $C_{1-22}$ alkylene, $C_{1-22}$ alkenyl, $C_{1-22}$ alkynyl and $C_{1-22}$ arylene, wherein the composition lacks a secondary therapeutic agent.

2. The composition of claim 1 wherein R is selected from the group consisting of methyl, ethyl, propyl, butyl, hexyl, heptyl, octyl, dodecyl, 1-pentadecyl, 1-heptadecyl, 1-hexadecyl, 1-octadecyl, isopropyl, sec-butyl, t-butyl, 2-methylbutyl, 2-pentyl, 3-pentyl, cyclopropyl, cyclobutyl, cyclopentyl and cyclohexyl, vinyl (ethenyl), 1-propenyl, i-butenyl, pentenyl, hexenyl, n-decenyl, —$CH_2$—$CH_2$—COOH and c-pentenyl.

3. The composition of claim 1 wherein said CAP is selected from the group consisting of capsaicin, civamide, homocapsaicin, nordihydrocapsaicin, dihydrocapsaicin, homodihydrocapsaicin, n-vanillyloctanamide, nonivamide and n-vanillyldecanamide.

4. The composition of claim 1, wherein said esterified capsaicinoid is selected from the group consisting of capsaicin palmitate (palmitoyl capsaicin) and capsaicin stearate (stearoyl capsaicin).

5. The composition of claim 1, wherein said composition is formulated for oral administration.

6. The composition of claim 5, wherein said composition further comprises one or more antioxidants.

7. The composition of claim 6, wherein the antioxidant is selected from the group consisting of ascorbic acid, sodium ascorbate, ascorbyl palmitate, sodium bisulfite, sodium metabisulfate, curcumin, curcumin derivatives, ursolic acid, resveratrol, resveratrol derivatives, alpha-lipoic acid and monothioglycerol.

8. The composition of claim 5, wherein the composition comprises one or more acceptable polysaccharides.

9. The composition of claim 8, wherein the polysaccharide is dextran sulfate, pectin, modified pectin, insoluble 1,3-β-D glucan, micronized 1,3-β-D glucan, soluble 1,3-β-D glucan, phosphorylated 1,3-β-D glucan, aminated 1,3-β-D glucan and carboxymethylated 1,3-β-D glucan, sulfated 1,3-β-D glucan, insoluble 1,3/1,6-β-D glucan, micronized 1,3/1,6-β-D glucan, soluble 1,3/1,6-β-D glucan, phosphorylated 1,3/1,6-β-D glucan, aminated 1,3/1,6-β-D glucan and carboxymethylated 1,3/1,6-β-D glucan or sulfated 1,3/1,6-β-D glucan.

10. The composition of claim 5, wherein the dietary supplement composition comprises from 0.025% to 20% by weight of the esterified capsaicinoid.

11. The composition of claim 10, wherein the dietary supplement composition comprises from 0.05% to 20% by weight of the esterified capsaicinoid.

12. The composition of claim 10, wherein the dietary supplement composition comprises from 0.05% to 10% by weight of the esterified capsaicinoid.

13. The composition of claim 1, wherein said composition comprises from about 5 to 25 mg of said esterified capsaicinoid.

14. The composition of claim 1, wherein said composition comprises one or more additional nutraceutical or dietary supplement agents.

15. The composition of claim 1, wherein said composition further comprises one or more acceptable preservatives or buffering agents.

16. The composition of claim 15, wherein the composition comprises a buffering agent, wherein the buffering agent is selected from the group consisting of monobasic and dibasic sodium phosphate, sodium benzoate, potassium benzoate, sodium citrate, sodium acetate and sodium tartrate.

17. The composition of claim 15, wherein the wherein the composition comprises a preservative, wherein the preservative is methylparaben, methylparaben sodium, propylparaben, propylparaben sodium, benzalkonium chloride or benzthonium chloride.

* * * * *